(12) United States Patent
Langguth et al.

(10) Patent No.: US 8,962,013 B2
(45) Date of Patent: *Feb. 24, 2015

(54) MULTI-LAYERED TRANSDERMAL SYSTEM WITH TRIAZINE UV ABSORBER

(75) Inventors: Thomas Langguth, Jena (DE); Stefan Bracht, Glienicke Nordbahn (DE)

(73) Assignee: Bayer Intellectual Property GmbH, Berlin (DE)

( * ) Notice: Subject to any disclaimer, the term of this patent is extended or adjusted under 35 U.S.C. 154(b) by 1144 days.

This patent is subject to a terminal disclaimer.

(21) Appl. No.: 11/416,148

(22) Filed: May 2, 2006

(65) Prior Publication Data

US 2006/0246122 A1  Nov. 2, 2006

Related U.S. Application Data

(60) Provisional application No. 60/676,788, filed on May 2, 2005.

(30) Foreign Application Priority Data

May 2, 2005  (EP) .................................... 05009579

(51) Int. Cl.
| | | |
|---|---|---|
| *A61K 9/70* | (2006.01) | |
| *A61K 31/53* | (2006.01) | |
| *A61K 31/56* | (2006.01) | |
| *A61K 31/57* | (2006.01) | |
| *A61K 31/565* | (2006.01) | |

(52) U.S. Cl.
CPC ............... *A61K 9/703* (2013.01); *A61K 9/7053* (2013.01); *A61K 31/565* (2013.01); *A61K 9/7038* (2013.01); *A61K 9/7061* (2013.01); *A61K 9/7084* (2013.01); *A61K 31/53* (2013.01); *A61K 31/57* (2013.01)
USPC ........... 424/449; 424/443; 424/448; 514/171; 514/241

(58) Field of Classification Search
None
See application file for complete search history.

(56) References Cited

U.S. PATENT DOCUMENTS

| | | | |
|---|---|---|---|
| 5,023,084 | A | 6/1991 | Chien et al. |
| 5,106,891 | A | 4/1992 | Valet |

(Continued)

FOREIGN PATENT DOCUMENTS

| | | |
|---|---|---|
| CA | 2372710 | 8/2000 |
| CA | 2 366 859 | 9/2001 |

(Continued)

OTHER PUBLICATIONS

Ciba Specialty Chemicals Tinosorb S brochure (2002).*

(Continued)

*Primary Examiner* — Kevin S Orwig
(74) *Attorney, Agent, or Firm* — Millen, White, Zelano & Branigan, P.C.

(57) ABSTRACT

The UV-stable solid transdermal therapeutic system (TTS) with UV absorber for photosensitive active pharmaceutical ingredients has a backing layer (1), at least one active ingredient-containing matrix (2), and a detachable protective film (3). Optionally an adhesive layer (4) and a separating layer (5) are introduced between the backing layer (1) and the at least one active ingredient-containing matrix (2). At least one hydroxyphenyltriazine compound acting as UV absorber is embedded in the backing layer (1), in the active ingredient-containing matrix (2), or in the adhesive layer (4). The TTS according to the invention achieves high stability at low concentrations of UV absorber, preferably 0.5 to 3% (m/m), so as to reduce or avoid skin irritation.

35 Claims, 2 Drawing Sheets

(56) References Cited

U.S. PATENT DOCUMENTS

| | | | |
|---|---|---|---|
| 5,128,124 | A | 7/1992 | Fankhauser et al. |
| 5,128,284 | A | 7/1992 | Olson et al. |
| 5,248,676 | A | 9/1993 | Nakagawa et al. |
| 5,352,457 | A | 10/1994 | Jenkins et al. |
| 5,376,377 | A | 12/1994 | Gale et al. |
| 5,512,292 | A | 4/1996 | Gale et al. |
| 5,538,736 | A | 7/1996 | Hoffmann et al. |
| 5,560,922 | A | 10/1996 | Chien et al. |
| 5,762,956 | A | 6/1998 | Chien et al. |
| 5,788,984 | A * | 8/1998 | Guenther et al. .......... 424/449 |
| 5,858,394 | A | 1/1999 | Lipp et al. |
| 5,866,157 | A | 2/1999 | Higo et al. |
| 5,904,931 | A * | 5/1999 | Lipp et al. .......... 424/449 |
| 5,906,830 | A | 5/1999 | Farinas et al. |
| 5,948,433 | A | 9/1999 | Burton et al. |
| 6,071,531 | A | 6/2000 | Jona et al. |
| 6,143,319 | A | 11/2000 | Meconi et al. |
| 6,238,284 | B1 | 5/2001 | Dittgen et al. |
| 6,521,250 | B2 | 2/2003 | Meconi et al. |
| 6,902,741 | B1 | 6/2005 | Grawe et al. |
| 6,924,410 | B2 * | 8/2005 | Tsuruda et al. .......... 602/48 |
| 7,470,452 | B1 | 12/2008 | Flosbach et al. |
| 7,687,554 | B2 | 3/2010 | Schellenberg et al. |
| 8,173,592 | B1 | 5/2012 | Engel et al. |
| 2002/0004065 | A1 | 1/2002 | Kanios et al. |
| 2003/0149385 | A1 | 8/2003 | Tsuruda et al. |
| 2003/0152616 | A1 | 8/2003 | Hartwig et al. |
| 2004/0009200 | A1 * | 1/2004 | Seyler et al. .......... 424/401 |
| 2004/0022836 | A1 | 2/2004 | Degen et al. |
| 2005/0055975 | A1 | 3/2005 | Tackett et al. |
| 2005/0129756 | A1 * | 6/2005 | Podhaisky et al. .......... 424/464 |
| 2005/0142175 | A1 | 6/2005 | Langguth et al. |
| 2005/0175678 | A1 | 8/2005 | Breitenbach |
| 2006/0246122 | A1 | 11/2006 | Langguth et al. |
| 2006/0251707 | A1 | 11/2006 | Schumacher et al. |
| 2008/0063698 | A1 | 3/2008 | Hartwig et al. |

FOREIGN PATENT DOCUMENTS

| | | |
|---|---|---|
| CA | 2 605 112 | 11/2006 |
| DE | 43 36 299 | 5/1995 |
| DE | 44 03 487 | 8/1995 |
| DE | 199 06152 | 8/2000 |
| DE | 199 12 623 | 9/2000 |
| DE | 100 53 375 | 1/2002 |
| EP | 0 285 563 | 10/1988 |
| EP | 0 483 370 | 5/1992 |
| EP | 0 787 488 | 8/1997 |
| EP | 1 121 941 | 8/2001 |
| EP | 1 197 212 | 4/2002 |
| EP | 1 269 999 | 1/2003 |
| EP | 1 452 173 | 9/2004 |
| EP | 1 541 137 | 6/2005 |
| JP | 59039827 | 3/1984 |
| JP | 60 069014 | 4/1985 |
| JP | 60166611 | 8/1985 |
| JP | 6 93217 | 4/1994 |
| JP | 09 315957 | 12/1997 |
| JP | 10-265371 | 10/1998 |
| JP | 10265371 | 10/1998 |
| JP | 2002 541122 | 12/2000 |
| JP | 530118 | 3/2004 |
| JP | 4 504109 | 1/2006 |
| WO | WO-90 04397 | 5/1990 |
| WO | WO-90 06736 | 6/1990 |
| WO | WO-92 07590 | 5/1992 |
| WO | WO-96 40355 | 12/1996 |
| WO | WO-97 38354 | 10/1997 |
| WO | WO-97 39743 | 10/1997 |
| WO | WO-99 66908 | 12/1999 |
| WO | WO-00 45797 | 8/2000 |
| WO | 00/56289 | 9/2000 |
| WO | WO-00 59542 | 10/2000 |
| WO | WO-01 37770 | 5/2001 |
| WO | WO 01/68061 * | 9/2001 .......... A61K 9/70 |
| WO | 02/34200 | 5/2002 |
| WO | WO-02 45701 | 6/2002 |
| WO | WO-03 077925 | 9/2003 |
| WO | WO-2004 058247 | 7/2004 |
| WO | WO-2004 073696 | 9/2004 |
| WO | WO 2004/073696 A1 * | 9/2004 .......... A61K 9/70 |
| WO | WO-2005 023878 | 3/2005 |
| WO | WO-2005 058287 | 6/2005 |
| WO | WO-2006 117139 | 11/2006 |
| WO | WO-2010 042152 | 4/2010 |

OTHER PUBLICATIONS

Decker, C., et al. Prog. Org. Coatings, (1996), 29; pp. 81-87.*

Ye, Yijun, et al. Ciba Specialty Chemicals, Tarrytown NY (1997); 21 pgs.*

Eric Chatelain et al: "Photostabilization of Butyl Methoxydibenzoylmethane . . . " Photochemistry and Photobiology, 2001, 74 (3), pp. 401-406 (in English).

Brisaert M. and J.A. Plaizier-Vercammen. "Investigation on the Photostability of a Tretinoin Lotion and Stabilization With Additives." Proc. 2nd World Meeting on Pharmaceutical Technology, APGI/APV, Paris, 25/28, May 1998, pp. 1231-1232.

Sekisui Chem Co Ltd., "Transcutaneous Absorption Plaster," Patent Abstracts of Japan, Publication Date: Jun. 10, 1998; English Abstract of JP-10-265371.

Thomson Innovation, English Translation of Claims and Description, Retrieved from Thomson Innovation Record View on Jun. 14, 2010; English Abstract of DE4336299.

Thomson Innovation, English Translation of Claims and Description, Retrieved from Thomson Innovation Record View on Jun. 14, 2010; English Abstract of DE4403487.

Thomson Innovation, English Translation of Claims and Description, Retrieved from Thomson Innovation Record View on Jun. 14, 2010; English Abstract of DE19912623.

Hisamitsu Pharmaceut Co Inc., "Device for percutaneous therapy," Patent Abstract of Japan, Publication Date: Dec. 9, 1997; English Abstract of JP-09 315957.

English Translation of JP-10-265371. Title: Transcutaneous Absorption Plaster. Inventor: Wakiya Takeshi. Applicant: Sekisui Chemical Co Ltd Publication Date: Oct. 6, 1998. (Computer translation obtained from http://www4.ipdl.inpit.go.jp/cgi-bin/tran of Jun. 30, 2009).

Bharnason, N. H. et al., "Low doses of estradiol in combination with gestodene to prevent early postmenopausal bone loss," American Journal of Obstetrics and Gynecology, Sep. 2000, vol. 183, No. 3, pp. 550-560.

Sitruk-Ware, R. et al., "Transdermal Application of Steroid Hormones for Contraception," J. Steroid Biochem. Molec. Biol., 1995, vol. 53, No. 1-6, pp. 247-251.

Thomas Innovation, English Abstract of WO-1990 04397.

Thomas Innovation, English Abstract of WO-2000 056289.

Thomson Innovation, English Abstract of EP-1 452 173, (2004).

Sanken Kako KK, "Production of dibenxyls," Patent Abstract of JP 10-265371 (1998).

Translation of Abstract of JP-10265371, Publication Date: Oct. 6, 1998.

Translation of Abstract of JP-60 069014, Publication Date: Apr. 19, 1985.

Translation of Abstract of JP-60166611, Publication Date: Aug. 29, 1985.

European Search Report dated May 12, 2004.

Partial European Search Report dated Sep. 27, 2005.

Translation of Abstract of JP-59039827, Publication Date: Mar. 5, 1984.

Translation of Abstract of JP-530118, Publication Date: Mar. 10, 2004.

Shinyosha: KK, "Image Display Apparatus and Pixel Constituent," Patent Abstracts of Japan, Publication Date: Jan. 5, 2006; English Abstract of JP-4 504 109.

* cited by examiner

MULTI-LAYERED TRANSDERMAL SYSTEM WITH TRIAZINE UV ABSORBER

CROSS-REFERENCE

The invention described and claimed hereinbelow is also described in U.S. Provisional Patent Application 60/676,788, filed May 2, 2005, and also in European Patent Application No. 05009579.3, also filed May 2, 2005. The aforesaid US Provisional Patent Application, whose subject matter is incorporated here by reference, provides the basis for a claim of priority of invention under 35 U.S.C. 119 (e).

BACKGROUND OF THE INVENTION

The invention is a solid transdermal therapeutic system with UV absorber. The UV-stable transdermal therapeutic system (TTS) is particularly designed for photosensitive active pharmaceutical ingredients. It comprises a backing layer 1, of at least one active ingredient-containing matrix 2, and of a detachable protective film 3. However an adhesive layer 4 and a separating layer 5 can optionally be introduced between the backing layer 1 and the active ingredient-containing matrix 2. At least one hydroxyphenyltriazine acting as UV absorber can be embedded in the backing layer 1, in the active ingredient-containing matrix 2, or in the adhesive layer 4.

Transdermal therapeutic systems, which contain a gestagen and/or an estrogen, are suitable for controlling fertility.

Attempts to employ photosensitive active ingredients, which absorb UV-A and UV-B rays, customarily used in sun creams, are known, as described by Briscart & Plaizier-Vercammen (Proc. $2^{nd}$ World Meeting on Pharmaceutics, Biopharmaceutics and Pharmaceutical Technology, APGI/APV, 1998, 1231-1232).

The patent literature further discloses the protection of transdermal therapeutic systems (TTS) provided with photosensitive active ingredients by visually conspicuous aluminized or lacquered covering films as backing layers of the TTS.

WO-A1-00/56289 describes a method for protecting therapeutic preparations, systems or their constituents, the intention being to achieve in each case specific protection from degradation by harmful factors, such as atmospheric oxygen, water, and/or light. Photo-protective substances, which absorb or reflect electromagnetic waves, are used, employing respectively absorbents or reflectants whose absorption or reflection spectrum covers the wave-length range responsible for the instability of the photosensitive substance or its constituents. Colored plastic films are used, inter alia, in this case as covering film, indicated by example of the 1,4-dihydopyridine derivative lacidipine.

The coloring of highly flexible plastic films proves to be difficult and does not provide reliable photo-protection owing to the frequently occurring fissures in the colored layer of the plastic film.

WO-A2-02/34200 further discloses transdermal therapeutic systems (TTS), which consist of an active ingredient-containing polymer matrix and of a backing layer. The polymer matrix and the backing layer are firmly connected or form a laminate. Both the polymer matrix and the backing layer comprise a colorless system, which absorbs in the UV range but has no intrinsic pharmacological effect. EP-A1-1452173 describes transdermal therapeutic systems, which consist of a backing layer, of at least one active ingredient-containing matrix and optionally of a detachable film and comprises a UV absorber. At least one UV absorber-containing adhesive layer is provided between the backing layer and the active ingredient-containing matrix furthest away from the surface of the skin. In addition, at least one separating layer, which is impermeable to active ingredient and impermeable to the UV absorber, is present between the adhesive layer containing the UV absorber and the active ingredient-containing matrix, which is furthest away from the surface of the skin. The UV absorber can be p-aminobenzoic acid, an aminobenzoic acid derivative, preferably 2-ethylhexyl 4-dimethyl-amino-benzoate and/or polyethoxyethyl 4-bis-(polyethoxyl)amino-benzoate, cinnamic acid, a cinnamic acid derivative, preferably isoamyl 4-methoxycinnamate or 2-ethylhexyl 4-methoxycinnamate, 3-benzylidenebornan-2-one, a benzylidene bornan-2-one derivative, preferably 3-(4')-methylbenzylindenebornan-2-one, 3-(4-sulphone)-benzylidenebornan-2-one, or 3-(4'-trimethylammonium)-benzylidenebornan-2-one methylsulphate, salicylic acid derivative, preferably 4-isopropyl-benzyl salicylate, 2-ethylhexyl salicylate, or 3,3,5-trimethyl-cyclohexyl salicylate, a benzotriazole, preferably 2-(5-chloro-2H-benzotriazol-2-yl)-6-(1,1-dimethylethyl)-4-methyl-phenol, 2,4,6'-trianiline-p-(carbo-2'-ethylhexyl-1'-oxy)-1,3,5-triazine, 3-imidazol-4-yl-acrylic acid, 3-imidazol-4-yl-3-imidazol-4-yl-acrylic ester, 2-phenylene benzimidazole-5-sulphonic acid, or its K, Na and triethanolamine (=TEA) salt, 2-cyano-3, 3-diphenylacrylic acid, terephthaloylidene-dicamphorsulphonic acid, butyl-methoxy-dibenzoylmethane, benzophenone, or a benzophenone derivative, preferably benzophenone-3 or benzophenone4.

The known solutions have the disadvantage
that the protective effect produced by the added UV absorber for the active ingredient is incomplete,
that owing to the incomplete protective effect in some cases higher concentrations of UV absorbers must be employed, which may have adverse effects on the compatibility of the TTS with skin.

SUMMARY OF THE INVENTION

It is therefore an object of the invention to provide a pharmaceutical preparation of the above-described kind with a UV absorber, which is provided with a photosensitive active ingredient, which is to be transdermally administered, and which ensures an increased protective effect for the active ingredient while using a minimum UV absorber concentration, so that the aforementioned disadvantages are avoided.

This object is achieved according to the invention by a solid transdermal therapeutic system (TTS) with a UV absorber, wherein the UV-stable TTS comprises a sequence of at least three layers, namely a backing layer 1, at least one active ingredient-containing matrix 2, and a detachable protective film 3. Optionally an adhesive layer 4 and a separating layer 5 can be introduced between the backing layer 1 and the at least one active ingredient-containing matrix 2. In the transdermal therapeutic system according to the invention the UV absorber comprises at least one hydroxyphenyltriazine compound and the UV absorber is embedded in the backing layer 1, in the active ingredient-containing matrix 2, or in the adhesive layer 4.

BRIEF DESCRIPTION OF THE DRAWING

The objects, features and advantages of the invention will now be illustrated in more detail with the aid of the following detailed description and examples of the invention, with reference to the accompanying figures, in which.

DETAILED DESCRIPTION OF THE INVENTION

Figure 1:
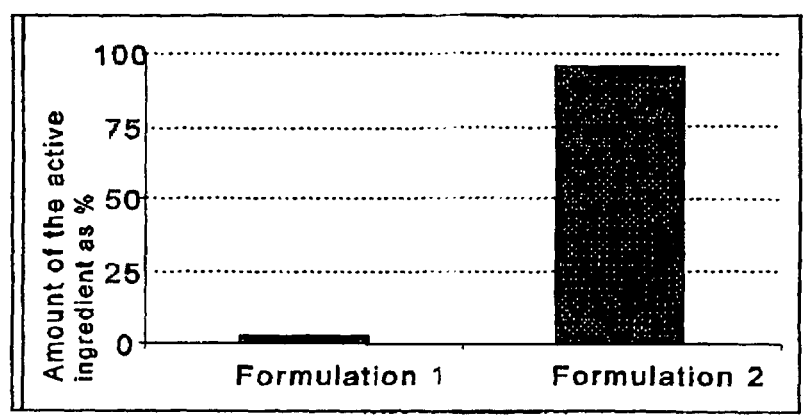
FIG. 1 is a graphical illustration showing the percentage of photosensitive active ingredient remaining in a transdermal therapeutic system according to the invention with photoprotective features and the percentage of photosensitive active ingredient remaining in a comparative transdermal therapeutic system.
Figure 2:
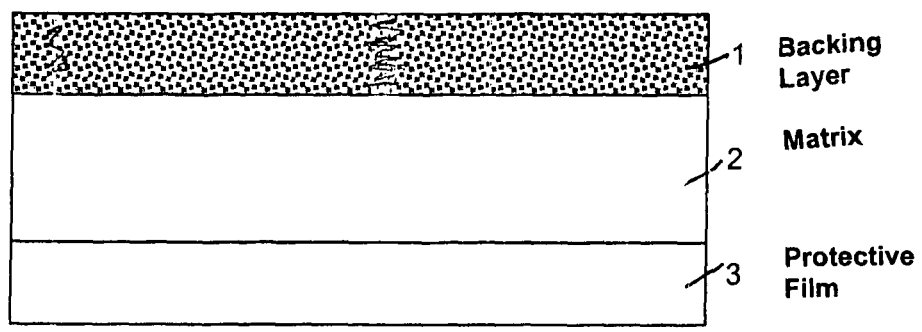
FIGS. 2 to 4 are respective diagrammatic cross-sectional views through various embodiments of the transdermal therapeutic systems according to the invention.
Figure 3:
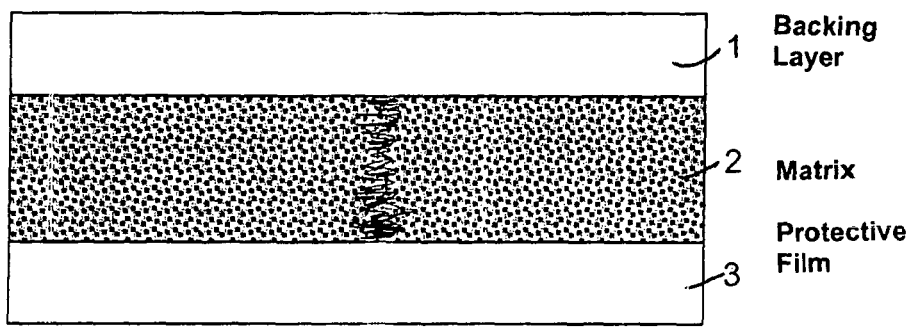
Figure 4:
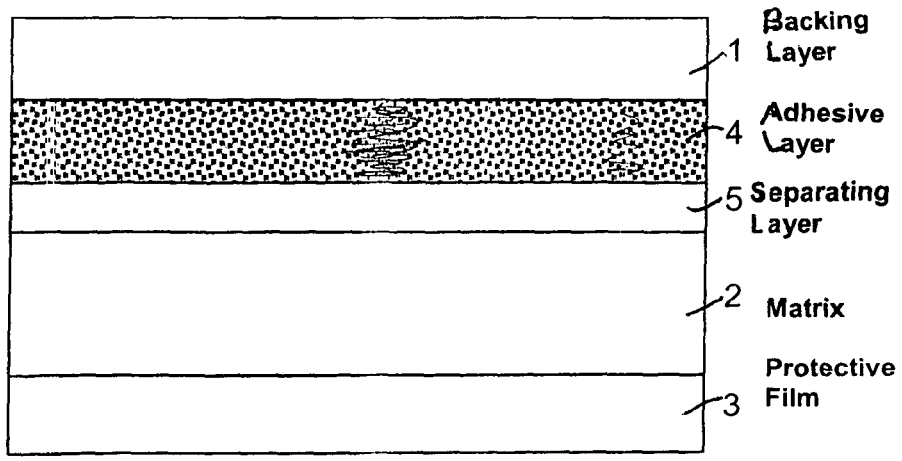

In a preferred embodiment according to the invention the UV absorber is 2,4-bis-([4-(2'-ethylhexyloxy)-2-hydroxy]phenyl)-6-(4-methoxyphenyl)-(1,3,5)-triazine.

In various embodiments of the transdermal therapeutic systems according the weight per unit area of the matrix 2 is from 30 to 150 g/m$^2$. In this connection, a weight per unit area of from 50 to 120 g/m$^2$ is preferred, and of 100 g/m$^2$ is particularly preferred.

Similarly in various embodiments of the solid transdermal therapeutic system according to the invention the weight per unit area of the adhesive layer 4 is from 5 to 50 g/m$^2$. In this connection, a weight per unit area of from 20 to 30 g/m$^2$ is preferred.

The UV absorber can be present according to the invention in the adhesive layer 4 in a concentration of from 0.5 to 5% (m/m) in dissolved form. In this connection, a concentration of from 1.0 to 4.0% is preferred, and of from 1.5 to 3.0% is particularly preferred.

Furthermore the matrix 2 and/or the adhesive layer 4 in the solid transdermal therapeutic system can be designed according to the invention to be self-adhesive and can consist substantially of polymers, which are selected from the group consisting of polyisobutylene, polybutene, polyacrylate, polydimethylsiloxane, styrene-isoprene block polymer and polyisoprene.

Preferred embodiments of the solid transdermal therapeutic systems according to the invention have a separating layer thickness of from 4 to 23 µm. In this connection, a layer thickness of from 4 to 10 µm is preferred.

In the solid transdermal therapeutic systems according to the invention the separating layer 5 is preferably impermeable to the active ingredient and impermeable to the UV absorber.

In preferred embodiments of the invention the separating layer 5 can consist of a barrier polymer. Preference is given in this connection to polyethylene terephthalate, polyacrylonitrile, polyvinyl chloride, polyvinylidene chloride, or its copolymers or co-laminates.

In preferred embodiments of the solid transdermal therapeutic system according to the invention the backing layer 1 is permeable to active ingredient and consists of polypropylene, of polyethylene, of polyurethane, of ethylene-vinyl acetate copolymer, or of a multilayer composite of these materials with one another or with other materials.

The UV absorber(s) in the solid transdermal therapeutic system according to the invention can be colorless or yellowish.

It is furthermore possible for the solid transdermal therapeutic system according to the invention to be transparent or slightly opaque.

The active ingredient in the solid transdermal therapeutic system according to the invention can be at least one hormone.

The active pharmaceutical ingredient according to the invention can be a progestogen, preferably gestodene or levonorgestrol. Furthermore an estrogen, preferably ethinyl estradiol, can be added to the progestogen in the solid transdermal therapeutic system according to the invention.

According to the invention the solid transdermal therapeutic system can also be used to control fertility.

It is also possible according to the invention for the solid transdermal therapeutic system to be equipped without a membrane controlling active ingredient release.

The transdermal therapeutic system according to the invention has the following advantages compared with conventional systems with photosensitive active ingredient content.

The protective effect provided by the hydroxyphenyltriazine compounds acting as UV absorber is enhanced.

The concentration of the hydroxyphenyltriazine compounds acting as UV absorber, which is necessary to achieve a protective effect is reduced.

It is thus possible in particular to avoid or reduce the risk of possible skin irritation.

The invention is further illustrated and explained by the following examples.

EXAMPLE 1

Two formulations (1 and 2) of a photosensitive active ingredient from the progestogens were prepared. Formulation 2 comprises an adhesive layer 4 and a separating layer 5, and the adhesive layer comprises 2.5% by weight of a UV-absorbing substance from the hydroxyphenyltriazine compounds. Formulation 1 has no adhesive layer and no separating layer. Formulation 1 serves as comparative formulation. Both formulations comprise an active ingredient-containing matrix 2 with a photosensitive progestogen and are equipped with a backing layer 1 of polyethylene, resulting in a TTS in each case. Formulation 2 has the following composition:

1. Active ingredient-containing matrix:
   1.9% progestogen
   98.1% polyisobutylene-based adhesive;
2. Adhesive layer:
   3% Tinosorb®S
   97% polyisobutylene-based adhesive.

Tinosorb®S (from Ciba, Lampertheim) is a UV absorber of the hydroxyphenyltriazine class.

To investigate the photo-protective effect, both formulations were irradiated with light having a UV spectrum of 300-800 nm for a period of up to 34 h. The radiation source used was a xenon lamp. A filter system (type: Suprax® filter) was placed between the radiation source and the samples to be irradiated in order to simulate irradiation under realistic conditions of use of the TTS. The active ingredient content in the TTS after irradiation was then determined.

FIG. 1 reveals that the TTS of formulation 2, which comprised an adhesive layer with UV-absorbing substance and a separating layer, still comprised about 95% of the originally employed amount of the photosensitive active ingredient after irradiation for 34 h, whereas the TTS of formulation 1 comprised only about 3% of the originally employed amount of the photosensitive active ingredient after irradiation.

The system according to the invention has improved protection from the sun under realistic conditions-of-use, since the UV-protective effect of the system according to the invention (formulation 2) was considerably greater than that of the comparative system (formulation 1).

EXAMPLE 2

The formulations of example 2 have a photosensitive active ingredient from the progestogens, and in each case an adhesive layer and separating layer. The separating layer in each of these formulations consists of polyethylene terephthalate (Hostaphan®[1] from Mitsubishi Polyester, Wiesbaden). Each formulation has the following composition:
1. Active ingredient-containing matrix
   1.9% progestogen
   98.1% polyisobutylene-based adhesive;
2. Adhesive layer 1 and 2:
   2.5% Tinosorb®S
   97.5% polyacrylate-based adhesive.

EXAMPLE 3

The formulations of example 3 have a photosensitive active ingredient from the progestogens, and in each case two adhesive layers and separating layers. The separating layers in each case consist of polyethylene terephthalate (Hostaphan®[1] from Mitsubishi Polyester, Wiesbaden). These formulations each have the following composition:
1. Active ingredient-containing matrix:
   1.9% progestogen
   98.1% polyisobutylene-based adhesive;
2. Adhesive layer 1 and 2:
   3% Tinuvin®400
   97% polyacrylate-based adhesive.
Tinuvin®400 (from CIBA, Lampertheim) is a UV absorber of the hydroxyphenyltriazine class.

EXAMPLE 4 TO 12

The formulations of example 4 have a photosensitive active ingredient from the progestogens, and in each case at least one adhesive layer and separating layer. In these formulations in which the active ingredient-containing matrix is embodied analogous to examples 1 to 3 and the adhesive layer comprises a poly-isobutylene-based adhesive and has the compositions mentioned below.

| Composition of the adhesive layer | Example | | | | | | | | |
|---|---|---|---|---|---|---|---|---|---|
| | 4 | 5 | 6 | 7 | 8 | 9 | 10 | 11 | 12 |
| Tinosorb ® S [%] | 2 | 2 | 2 | 3 | 3 | 3 | 4 | 4 | 4 |
| Polyisobutylene-based adhesive [%] | 98 | 98 | 98 | 97 | 97 | 97 | 96 | 96 | 96 |
| Weight per unit area [g/m$^2$] | 20 | 30 | 50 | 20 | 30 | 50 | 20 | 30 | 50 |

EXAMPLE 13 TO 21

The formulations of examples 13 to 21 have a photosensitive active ingredient from the progestogens, and in each case at least one adhesive layer and separating layer. The active ingredient-containing matrix is embodied analogously to examples 1 to 3, and the adhesive layer comprises a polyacrylate-based adhesive and has the compositions mentioned below.

| Composition of the adhesive layer | Example | | | | | | | | |
|---|---|---|---|---|---|---|---|---|---|
| | 13 | 14 | 15 | 16 | 17 | 18 | 19 | 20 | 21 |
| Tinosorb ® S [%] | 2 | 2 | 2 | 3 | 3 | 3 | 4 | 4 | 4 |
| Polyacrylate-based adhesive [%] | 98 | 98 | 98 | 97 | 97 | 97 | 96 | 96 | 96 |
| Weight per unit area [g/m$^2$] | 20 | 30 | 50 | 20 | 30 | 50 | 20 | 30 | 50 |

While the invention has been illustrated and described as embodied in a solid transdermal therapeutic system with UV absorber, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:
1. A solid transdermal therapeutic system (TTS) with a UV absorber, said solid transdermal therapeutic system comprising a sequence of at least five layers;
   wherein said at least five layers comprise a backing layer (1), an adhesive layer (4), a separating layer (5), at least one active ingredient-containing matrix (2), and a detachable protective film (3);
   wherein the adhesive layer (4) is between the backing layer (1) and the separating layer (5), the separating layer (5) is between the adhesive layer (4) and the at least one active ingredient-containing matrix (2), and the at least one active ingredient-containing matrix (2) is between the separating layer (5) and the detachable protective film (3);
   wherein said UV absorber consists of 2,4-bis-([4-(2'-ethylhexyloxy)-2-hydroxy]phenyl)-6-(4-methoxyphenyl)-(1,3,5)-triazine as the sole UV absorber in the system, said UV absorber is present in a concentration of from 0.5 to 2.0% (m/m) in dissolved form in the adhesive layer and said UV absorber is also optionally present in the backing layer (1);
   wherein said active pharmaceutical ingredient comprises at least one hormone; and
   wherein the solid transdermal therapeutic system is transparent.
2. The solid transdermal therapeutic system as defined in claim 1, wherein the at least one active ingredient-containing matrix (2) has a weight per unit area of from 30 to 150 g/m$^2$.
3. The solid transdermal therapeutic system as defined in claim 2, wherein the weight per unit area of the at least one active ingredient-containing matrix (2) is from 50 to 120 g/m$^2$.
4. The solid transdermal therapeutic system as defined in claim 1, wherein the adhesive layer (4) has a weight per unit area of from 5 to 50 g/m$^2$.
5. The solid transdermal therapeutic system as defined in claim 4, wherein the weight per unit area of the adhesive layer (4) is from 20 to 30 g/m$^2$.
6. The solid transdermal therapeutic system as defined in claim 1, wherein the at least one active ingredient-containing matrix (2) and the adhesive layer (4) are self-adhesive and comprise at least one polymer;
   wherein said at least one polymer is selected from the group consisting of polyisobutylene, polybutene, polyacrylate, polydimethylsiloxane, styrene-isoprene block polymers and polyisoprene.
7. The solid transdermal therapeutic system as defined in claim 1, wherein said separating layer (5) has a layer thickness of from 4 to 23 μm.
8. The solid transdermal therapeutic system as defined in claim 7, wherein said layer thickness is from 4 to 10 μm.

9. The solid transdermal therapeutic system as defined in claim 1, wherein said at least one active ingredient-containing matrix (2) contains an active pharmaceutical ingredient and said separating layer (5) is impermeable to said active pharmaceutical ingredient and impermeable to said UV absorber.

10. The solid transdermal therapeutic system as defined in claim 1, wherein said separating layer (5) consists of a barrier polymer and said barrier polymer is polyethylene terephthalate, polyacrylonitrile, polyvinyl chloride, polyvinylidene chloride, or a copolymer or co-laminate thereof.

11. The solid transdermal therapeutic system as defined in claim 1, wherein said at least one active ingredient-containing matrix (2) contains an active pharmaceutical ingredient, said backing layer (1) is permeable to said active pharmaceutical ingredient and said backing layer (1) consists of polypropylene, polyethylene, polyurethane, ethylene-vinyl acetate copolymer, or a multilayer composite of the foregoing polymers with one another.

12. The solid transdermal therapeutic system as defined in claim 1, wherein said UV absorber is colorless or yellow.

13. The solid transdermal therapeutic system as defined in claim 1, wherein said active pharmaceutical ingredient is a progestogen.

14. The solid transdermal therapeutic system as defined in claim 13, wherein said progestogen is gestodene or levonorgestrel.

15. The solid transdermal therapeutic system as defined in claim 13, which is effective as a fertility controlling preparation.

16. The solid transdermal therapeutic system as defined in claim 1, wherein said active pharmaceutical ingredient comprises a progestogen and an estrogen.

17. The solid transdermal therapeutic system as defined in claim 16, which is effective as a fertility controlling preparation.

18. The solid transdermal therapeutic system as defined in claim 1, containing an active pharmaceutical ingredient and without a membrane controlling release of the active pharmaceutical ingredient.

19. The solid transdermal therapeutic system as defined in claim 1, wherein said separating layer comprises a polyethylene terephthalate.

20. The solid transdermal therapeutic system as defined in claim 1, wherein said backing layer comprises a polyethylene.

21. A solid transdermal therapeutic system (TTS) with a UV absorber, said solid transdermal therapeutic system comprising a sequence of at least five layers;
wherein said at least five layers comprise a backing layer (1), an adhesive layer (4), a separating layer (5), at least one active ingredient-containing matrix (2), and a detachable protective film (3);
wherein the adhesive layer (4) is between the backing layer (1) and the separating layer (5), the separating layer (5) is between the adhesive layer (4) and the at least one active ingredient-containing matrix (2), and the at least one active ingredient-containing matrix (2) is between the separating layer (5) and the detachable protective film (3);
wherein said UV absorber consists of 2,4-bis-([4-(2'-ethylhexyloxy)-2-hydroxy]phenyl)-6-(4-methoxyphenyl)-(1,3,5)-triazine as the sole UV absorber in the system, said UV absorber is present in a concentration of from 0.5 to 2.0% (m/m) in dissolved form in the adhesive layer and said UV absorber is also optionally present in the backing layer (1);
wherein the solid transdermal therapeutic system is transparent; and
wherein the active ingredient comprises gestodene and ethinyl estradiol.

22. The solid transdermal therapeutic system as defined in claim 21, wherein the at least one active ingredient-containing matrix (2) has a weight per unit area of from 30 to 150 g/m².

23. The solid transdermal therapeutic system as defined in claim 21, wherein the weight per unit area of the at least one active ingredient-containing matrix (2) is from 50 to 120 g/m².

24. The solid transdermal therapeutic system as defined in claim 21, wherein the adhesive layer (4) has a weight per unit area of from 5 to 50 g/m².

25. The solid transdermal therapeutic system as defined in claim 24, wherein the weight per unit area of the adhesive layer (4) is from 20 to 30 g/m².

26. The solid transdermal therapeutic system as defined in claim 21, wherein said UV absorber is present in the adhesive layer (4).

27. The solid transdermal therapeutic system as defined in claim 21, wherein the at least one active ingredient-containing matrix (2) and the adhesive layer (4) are self-adhesive and comprise at least one polyisobutylene polymer.

28. The solid transdermal therapeutic system as defined in claim 21, wherein said separating layer (5) has a layer thickness of from 4 to 23 μm.

29. The solid transdermal therapeutic system as defined in claim 28, wherein said layer thickness is from 4 to 10 μm.

30. The solid transdermal therapeutic system as defined in claim 21, wherein said at least one active ingredient-containing matrix (2) contains the active pharmaceutical ingredient and said separating layer (5) is impermeable to said active pharmaceutical ingredient and impermeable to said UV absorber.

31. The solid transdermal therapeutic system as defined in claim 21, wherein said separating layer (5) comprises a polyethylene terephthalate barrier polymer.

32. The solid transdermal therapeutic system as defined in claim 21, wherein said UV absorber is colorless or yellow.

33. The solid transdermal therapeutic system as defined in claim 21, which is effective as a fertility controlling preparation.

34. The solid transdermal therapeutic system as defined in claim 21, wherein said backing layer comprises a polyethylene.

35. The solid transdermal therapeutic system as defined in claim 1, wherein the at least one active ingredient-containing matrix (2) and the adhesive layer (4) are self-adhesive and comprise at least one polyisobutylene polymer.

* * * * *